United States Patent
Reichard et al.

(10) Patent No.: US 9,186,378 B2
(45) Date of Patent: Nov. 17, 2015

(54) SYSTEM AND METHOD FOR LOW SPEED CONTROL OF POLYPHASE AC MACHINE

(71) Applicant: ZBB Energy Corporation, Menomonee Falls, WI (US)

(72) Inventors: Jeffrey A. Reichard, Oconomowoc, WI (US); Nathan Jobe, Germantown, WI (US); Thomas Alan Laubenstein, Waukesha, WI (US)

(73) Assignee: EnSync, Inc., Menomonee Falls, WI (US)

( * ) Notice: Subject to any disclaimer, the term of this patent is extended or adjusted under 35 U.S.C. 154(b) by 401 days.

(21) Appl. No.: 13/720,709

(22) Filed: Dec. 19, 2012

(65) Prior Publication Data
US 2013/0155731 A1    Jun. 20, 2013

Related U.S. Application Data

(60) Provisional application No. 61/577,447, filed on Dec. 19, 2011.

(51) Int. Cl.
| | |
|---|---|
| *H02M 5/453* | (2006.01) |
| *A61K 33/24* | (2006.01) |
| *H02M 7/219* | (2006.01) |
| *H02J 3/38* | (2006.01) |
| *H02P 23/03* | (2006.01) |

(Continued)

(52) U.S. Cl.
CPC ............. *A61K 33/24* (2013.01); *A61K 49/005* (2013.01); *A61N 5/062* (2013.01); *H02J 3/386* (2013.01); *H02M 5/453* (2013.01); *H02M 7/219* (2013.01); *H02P 23/03* (2013.01); *Y02E 10/76* (2013.01); *Y02E 10/763* (2013.01)

(58) Field of Classification Search
CPC ....... H02M 5/453; H02M 7/219; F03D 7/026; F03D 7/0276; H02J 3/38
USPC ...................... 363/37; 290/44, 55; 322/22, 12
See application file for complete search history.

(56) References Cited

U.S. PATENT DOCUMENTS

| | | | | |
|---|---|---|---|---|
| 7,081,738 | B2 * | 7/2006 | Muramatsu et al. | 322/24 |
| 7,821,145 | B2 * | 10/2010 | Huang et al. | 290/31 |

(Continued)

FOREIGN PATENT DOCUMENTS

| | | |
|---|---|---|
| JP | 06009400 U | 2/1994 |
| JP | 2003299396 A | 10/2003 |

(Continued)

OTHER PUBLICATIONS

International Search Report and the Written Opinion of the International Searching Authority, dated Apr. 19, 2013 for Application No. PCT/2012/070694—(9 pages).

*Primary Examiner* — Jessica Han
(74) *Attorney, Agent, or Firm* — Boyle Fredrickson, S.C.

(57) ABSTRACT

A method of starting a wind turbine generator of any type of polyphase AC machine, including, but not limited to, brushless DC or permanent magnet machines is disclosed. The machine starts from a dead stop or from low speed operation and is accelerated to the cut in speed for power production. The start-up is realized utilizing the common set of electrical conductors and the power converter also used for capturing the generated power. Under initial operation, the power converter executes a PWM modulation technique to drive the machine. Periodically, the PWM modulation is stopped to read the electrical position of the generator.

9 Claims, 7 Drawing Sheets

(51) Int. Cl.
*A61K 49/00* (2006.01)
*A61N 5/06* (2006.01)

(56) References Cited

U.S. PATENT DOCUMENTS 8,013,459 B2 9/2011 Ito et al.
8,097,975 B2 * 1/2012 Bosch et al. ................ 307/10.1
8,115,330 B2 * 2/2012 Menke ........................... 290/44
2010/0171381 A1 7/2010 Ling
2013/0134711 A1 * 5/2013 Spruce ........................... 290/44

FOREIGN PATENT DOCUMENTS

| JP | 2008005663 A | 1/2008 |
| WO | 2004047284 A1 | 7/2004 |

* cited by examiner

SYSTEM AND METHOD FOR LOW SPEED CONTROL OF POLYPHASE AC MACHINE

CROSS-REFERENCE TO RELATED APPLICATIONS

This application claims priority to U.S. provisional application Ser. No. 61/577,447, filed Dec. 19, 2011, the entire contents of which is incorporated herein by reference.

BACKGROUND OF THE INVENTION

The subject matter disclosed herein relates to power converters and, more specifically, to improved control of and improved power conversion from polyphase alternating current (AC) machines during low speed operation.

In recent years, increased demands for energy and increased concerns about supplies of fossil fuels and their corresponding pollution have led to an increased interest in renewable energy sources. Two of the most common and best developed renewable energy sources are photovoltaic energy and wind energy. Other renewable energy sources may include fuel cells, hydroelectric energy, tidal energy, and biofuel or biomass generators. However, using renewable energy sources to generate electrical energy presents a new set of challenges.

Wind turbines, for example, provide a variable supply of energy. The supply is dependent on the amount of wind. Wind turbines are typically configured to generate AC energy and typically provide a multi-phase AC voltage at varying current levels. Due to the variable nature of the energy supplied, power converters are commonly inserted between the wind turbine and the utility gird or an electrical load, if operating independently of the utility grid. The power converters typically require that the wind turbine be rotating at a minimum speed, also known as a cut-in speed, such that it is generating a minimum level of power before the power converter begins operation.

However, wind turbines have substantial mass and require significant energy to accelerate from a stop to the cut-in speed such that the converter may begin to harvest energy. Further, some wind turbines may have an inertial "knee", meaning they require a greater amount of energy to overcome, for example, static friction forces and begin rotation than the amount of energy required to continue rotation of the turbine. The inertial "knee" may, therefore, require a higher initial wind speed to begin operation of the wind turbine, but once the initial speed has been obtained, operation could continue at lower wind speeds. As a result, the wind turbine may have a range of wind speeds at which it may be capable of generating energy but the energy is lost if the wind turbine was not already rotating. Similarly, the inertia of a wind turbine may cause slow acceleration from a stop even if the wind is strong enough to accelerate the turbine to the cut-in speed. The slow acceleration may result in an undesirable amount of time to accelerate the wind turbine up to the cut-in speed. During the acceleration, the wind turbine is again failing to produce energy during periods at which the wind speed is sufficient for energy generation.

In order to obtain the highest potential energy generation from the wind turbine, it is desirable to have the wind turbine operating above the cut-in speed of the converter as often as possible. Thus, it would be desirable to provide a system that can overcome the inertial "knee" and/or help accelerate the wind turbine up to the cut-in speed.

BRIEF DESCRIPTION OF THE INVENTION

The subject matter disclosed herein describes a system and method for controlling polyphase machines during low speed operation and, more specifically, a system and method for starting a polyphase AC machine having no position sensor coupled to the AC machine.

According to one aspect of the present invention, the invention provides a method of starting a wind turbine generator of any type of polyphase AC machine, including, but not limited to, brushless DC or permanent magnet machines. The machine starts from a dead stop or from low speed operation and is accelerated to the cut in speed for power production. The start-up is realized utilizing the common set of electrical conductors also used for capturing the generated power. Under initial operation, a PWM modulation technique drives the machine. Periodically, the PWM modulation is stopped to read the electrical position of the generator. Other applications, which require similar starting requirements, such as fly wheels, may similarly apply the starting method.

According to one embodiment of the invention, a power conversion system includes a set of terminals configured to connect the power conversion system to a polyphase AC machine, a DC bus having a positive rail and a negative rail, a power converter connected between the set of terminals and the DC bus and configured for bidirectional power transfer between the set of terminals and the DC bus, a memory device configured to store a series of instructions, and a controller. The controller is configured to execute the series of instructions to execute a start up control module below a predefined speed, where the start up control module controls rotation of the AC machine, and to execute a current regulator above the predefined speed to transfer power generated by the AC machine to the DC bus.

According to another aspect of the invention, the power conversion system includes an output configured to be connected to a utility grid and an inverter module connected between the output and the DC bus. The inverter module is configured for bidirectional power transfer between the output and the DC bus, and the controller is configured to control the inverter module to maintain a desired DC voltage on the DC bus when the start up control module is executing.

According to still another aspect of the invention, the power conversion system may include an energy storage device and a second power converter configured to transfer energy between the energy storage device and the DC bus. The controller is configured to control the second power converter to maintain a desired DC voltage on the DC bus when the start up control module is executing.

According to yet another aspect of the invention, the start up control module may include a modulation module configured to convert a voltage on the DC bus to an AC voltage for the AC machine. The controller is configured to periodically disable the modulation module, and when the modulation module is disabled, the controller is configured to read a back-emf voltage present on the AC machine.

According to another embodiment of the invention, a power conversion system includes a first set of terminals configured to connect the power conversion system to a polyphase AC machine, a DC bus having a positive rail and a negative rail, a plurality of first switches configured to selectively connect the first set of terminals to the DC bus, a second set of terminals configured to connect to a utility grid, a plurality of second switches configured to selectively connect the DC bus to the second set of terminals, a memory device configured to store a series of instructions, and a controller. The controller is configured to execute the instructions in a first operating mode and in a second operating mode. During the first operating mode, the controller generates a gating signal for each of the first and second switches to accelerate the AC machine to a predefined speed, and during the second operating mode, the controller generates the gating signal for each of the first and second switches to transfer energy generated by the AC machine to the utility grid. During the first operating mode, the first switches may be controlled to provide a multi-phase AC voltage at the first set of terminals, where the multi-phase AC voltage has a variable magnitude and a variable frequency to control a speed of the AC machine. The second switches are controlled to transfer energy between the utility grid and the DC bus to maintain a substantially constant DC voltage on the DC bus.

According to another aspect of the invention, the power conversion system also includes a plurality of voltage sensors generating a signal corresponding to an amplitude of voltage present at the first set of terminals. The controller is further configured to receive each of the signals from the voltage sensors, and during the first operating mode, the controller periodically disables the first switches and reads each of the signals when the first switches are disabled. During the second operating mode, the controller continually controls the first set of switches and reads the signals in tandem with controlling the first set of switches. The controller may be further configured to determine a back-emf voltage present at the first set of terminals as a function of the signals read from the voltage sensors, and to determine an electrical angle of the voltage present at the first set of terminals as a function of the back-emf voltage.

According to another embodiment of the invention, a method of accelerating a polyphase AC machine for use in a wind turbine up to a predefined initial speed greater than a cut-in speed of the wind turbine is disclosed. The method includes the steps of controlling a power converter in a first operating mode to execute a modulation module to generate a voltage for the AC machine, where the voltage has a variable magnitude and a variable frequency to control a rotational speed of the AC machine. During the first operating mode, the method disables the modulation module at a periodic interval and determines a back-emf voltage present on the AC machine when the modulation module is disabled. The rotational speed of the AC machine is determined as a function of the back-emf voltage. The power converter is controlled in a second operating mode when the rotational speed is greater than the predefined initial speed, and during the second operating mode, the power converter transfers energy from the AC machine to a DC bus in the power converter.

According to another embodiment of the invention, a power conversion system for transferring energy generated from an AC generation source to a utility grid includes a set of terminals configured to connect the power conversion system to the AC generation source, a DC bus having a positive rail and a negative rail, a power converter connected between the set of terminals and the DC bus and configured for power transfer between the set of terminals and the DC bus, a memory device configured to store a series of instructions, and a controller. The controller is configured to execute the series of instructions to execute a modulation module above a predefined speed for continuous modulation of the power converter to transfer power generated by the AC generation source to the DC bus and to periodically insert a blanking time in coordination with the modulation module below the predefined speed for intermittent modulation of the power converter to transfer power generated by the AC generation source to the DC bus.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Figure 1:
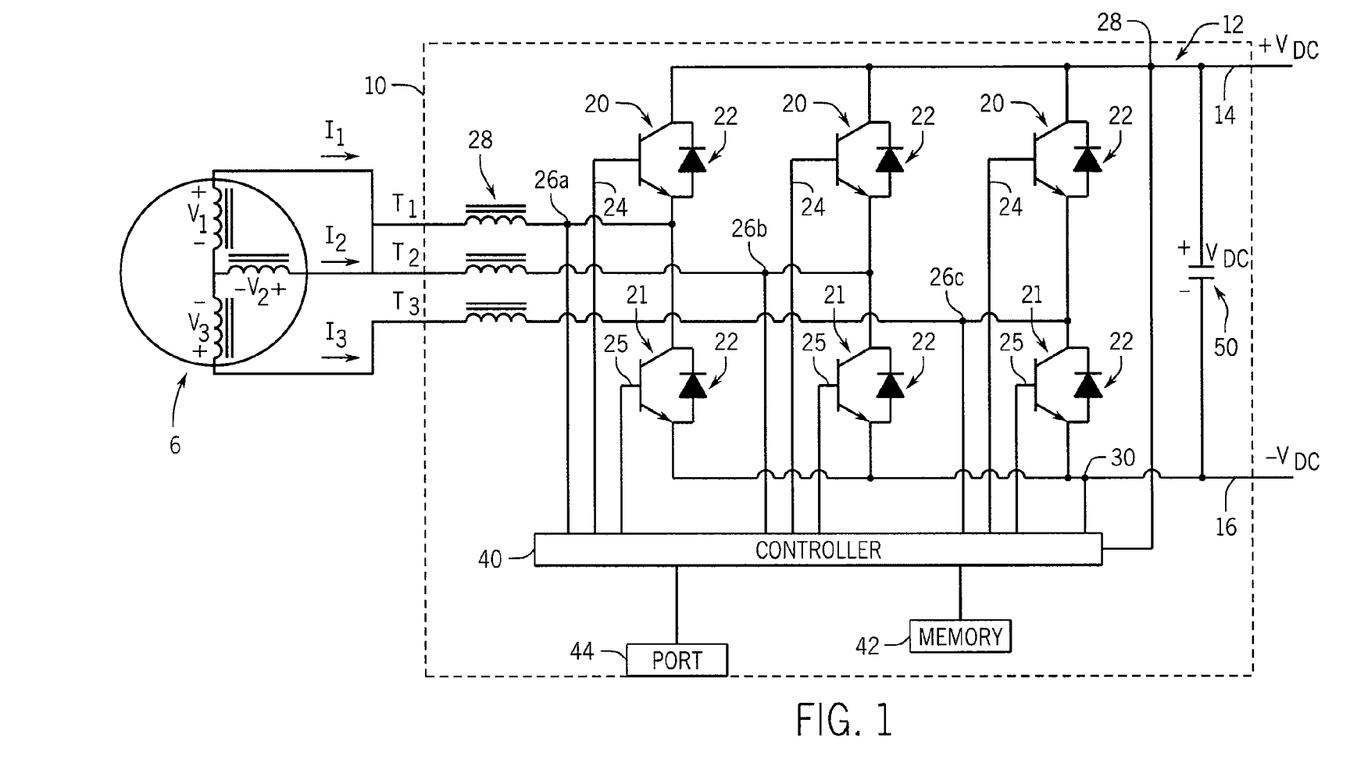
FIG. 1 is a schematic representation of a converter according to one embodiment of the invention.

Turning initially to FIG. 1, an exemplary power converter 10 incorporating one embodiment of the present invention is illustrated. The power converter 10 is configured for bidirectional power transfer between an alternator 6 connected to the power converter 10 and a DC bus 12 present in the power converter 10. The power converter 10 includes three input terminals, T1-T3, configured to be connected to the alternator 6. In one operating mode, each of the input terminals, T1-T3, of the illustrated embodiment is configured to transfer power from the alternator 6 to the DC bus 12 of the power converter 10. The alternator 6 may be driven by an external source, such as the wind, and generate, for example, three phase alternating current (AC) voltage, V1-V3, each phase connected to one of the input terminals. An input filter 28 is connected in series with each of the terminals, T1-T3. In another operating mode, the power converter 10 may be configured to convert the DC voltage present on the DC bus to a variable amplitude and variable frequency AC voltage on the terminals, T1-T3, controlling rotation of the alternator 6.

When the alternator 6 is generating power, the power converter 10 receives the multiphase AC input voltage, V1-V3, at the terminals, T1-T3, and outputs a desired DC voltage, Vdc, present on a DC bus 12 using switching devices, 20 and 21. The DC bus 12 includes a positive rail 14 and a negative rail 16 which are made available at outputs, +Vdc and −Vdc. As is understood in the art, the positive rail 14 and the negative rail 16 may conduct any suitable DC voltage potential with respect to a common or neutral voltage and are not limited to a positive or a negative DC voltage potential. Further, either of the positive rail 14 or the negative rail 16 may be connected to a neutral voltage potential. The positive rail 14 typically conducts a DC voltage having a greater potential than the negative rail 16.

The switching devices, 20 and 21, are typically solid-state power devices. FIG. 1 shows the switching devices, 20 and 21, as bipolar junction transistors (BJTs); however, it is contemplated that any suitable switching device according to the application requirements may be used, including, but not limited to, insulated gate bipolar transistors (IGBT), field effect transistors (FET), silicon controlled rectifiers (SCR), thyristors such as integrated gate-commutated thyristors (IGCT) or gate turn-off thyristors (GTO), or other controlled devices. A diode 22 is connected in parallel to each of the switching devices, 20 and 21, for reverse conduction across the switching device, 20 and 21, as required when the switching device, 20 and 21, is turned off. This diode 22 may also be a part of the semiconductor switch. For each phase of the input, a positive switch, 20, is connected between the input terminal, T1-T3, and the positive rail 14 of the DC bus 12, and a negative switch, 21, is connected between the input terminal, T1-T3, and the negative rail 16 of the DC bus 12. Each of the positive switching devices 20 are controlled by a positive gating signal 24 and each of the negative switching devices 21 are controlled by a negative gating signal 25. Each of the positive and negative gating signals, 24 or 25, is enabled or disabled to selectively permit conduction through the positive or negative switching devices, 20 or 21 respectively. A capacitance 50 is connected between the positive rail 14 and the negative rail 16 of the DC bus 12. The capacitance 50 may be a single capacitor or any number of capacitors connected in series or parallel according to the system requirements. The capacitance 50 is configured to reduce the magnitude of ripple voltage resulting from the voltage conversion between the input voltage and the DC bus 12.

A controller 40 executes a series of stored instructions to generate the gating signals, 24 and 25. The controller 40 receives feedback signals from sensors corresponding to the amplitude of the voltage and/or current at various points throughout the power converter 10. The locations are dependent on the specific control routines being executed within the controller 40. For example, input sensors, 26a-26c, may provide an amplitude of the voltage present at each input terminal, T1-T3. Optionally, an input sensor, 26a-26c, may be operatively connected to provide an amplitude of the current conducted at each input terminal, T1-T3. Similarly a current and/or a voltage sensor, 28 and 30, may be operatively connected to the positive rail 14 and the negative rail 16, respectively, of the DC bus 12. The controller 40 interfaces with a memory device 42 to retrieve the stored instructions and with a communication port 44 to communicate with external devices. The controller 40 is configured to execute the stored instructions to control the power converter 10 as described herein.

Figure 4:
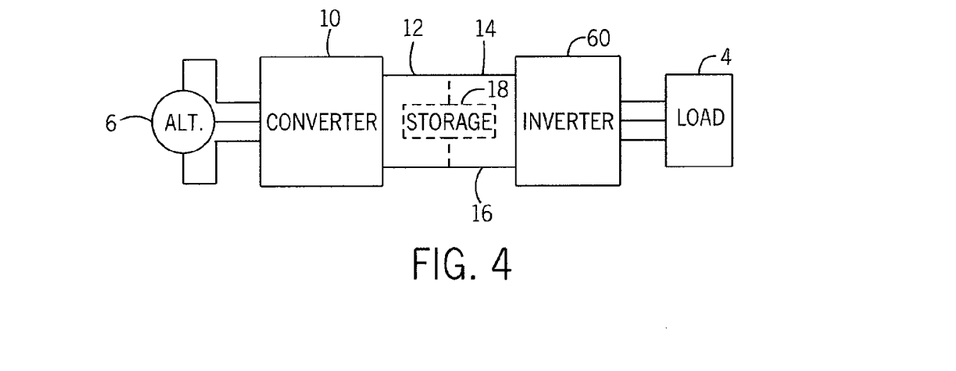
FIG. 4. is a block diagram representation of one embodiment of the invention.

Referring next to FIG. 4, an exemplary power conversion system includes a first power converter 10 and a second power converter, also referred to herein as an inverter, 60 connected by a DC bus 12. Optionally, an energy storage device 18 may be connected between the positive rail 14 and the negative rail 16 of the DC bus 12. The alternator 6, such as the generator of a wind turbine, supplies power to the power converter 10, which is converted to a DC voltage on the DC bus 12, and the inverter 60, in turn, supplies power to an electrical load 4 or to a utility grid (not shown) from the DC bus 12. The storage device 18 may also include a DC to DC converter to convert the DC voltage present on the DC bus 12 to a suitable DC voltage level according to requirements of the storage device. The storage device may be, for example, a lead-acid battery, a lithium ion battery, a zinc-bromide battery, a flow battery, or any other suitable energy storage device. The DC to DC converter operates to transfer energy between the DC bus 12 and the storage device 18 according to the application requirements.

Figure 2:
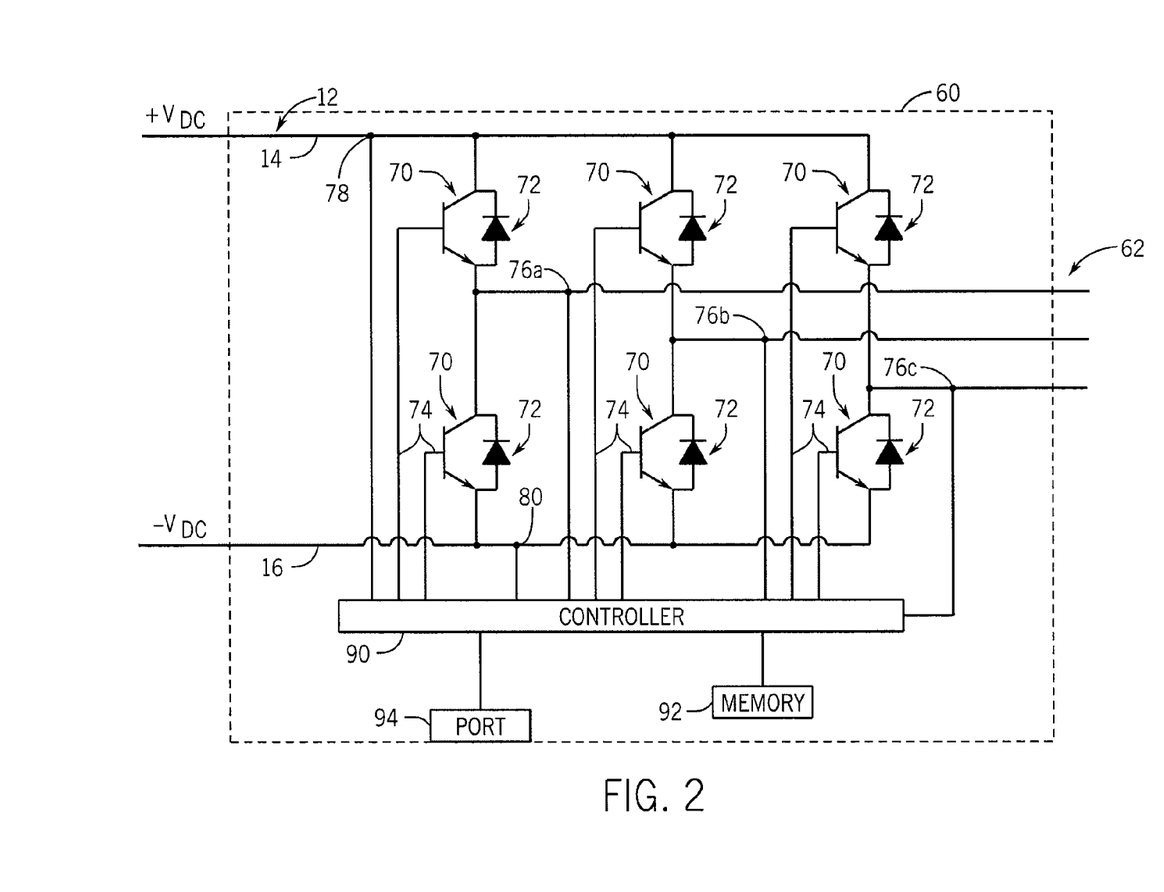
FIG. 2 is a schematic representation of an inverter according to one embodiment of the invention.

Referring now to FIG. 2, an exemplary inverter 60 is connected to the DC bus 12. the inverter 60 may be configured for bidirectional power transfer between the DC bus 12 and the utility grid. In one operating mode, the inverter 60 converts the DC voltage from the DC bus 12 to an AC voltage suitable to be supplied, for example, to the utility grid or an electrical load, such as a motor. In another operating mode, the inverter 60 may be configured to regulate the DC voltage present on the DC bus 12 by regulating current between the utility grid and the DC bus 12. Control of the inverter 60 in either operating mode is performed using switching devices 70 which selectively connect either the positive rail 14 or the negative rail 16 to one of the phases of the output 62. The switching devices 70 are typically solid-state power devices. FIG. 2 illustrates the switching devices 70 as bipolar junction transistors (BJTs); however, it is contemplated that any suitable switching device according to the application requirements may be used, including, but not limited to, insulated gate bipolar transistors (IGBT), field effect transistors (FET), silicon controlled rectifiers (SCR), thyristors such as integrated gate-commutated thyristors (IGCT) or gate turn-off thyristors (GTO), or other controlled devices. A diode 72 is connected in parallel to each of the switching devices 70 for reverse conduction across the switching device as required when the switching device 70 is turned off. This diode 72 may also be a part of the semiconductor switch. Each switching device 70 is controlled by a gating signal 74. The gating signal 74 is enabled or disabled to selectively permit conduction through the switching device 70.

A controller 90 executes a series of stored instructions to generate the gating signals 74. The controller 90 receives feedback signals from sensors corresponding to the amplitude of the voltage and/or current at various points throughout the inverter 60. The locations are dependent on the specific control routines being executed within the controller 90. For example, sensors, 76a-76c, may provide an amplitude of the voltage present at each phase of the output 62. Optionally, the sensors, 76a-76c, may be operatively connected to provide an amplitude of the current conducted at each phase of the output 62. Similarly a current and/or a voltage sensor, 78 and 80, may be operatively connected to the positive rail 12 and the negative rail 16, respectively, of the DC bus 12. The controller 90 interfaces with a memory device 92 to retrieve the stored instructions and with a communication port 94 to communicate with external devices. According to one embodiment of the invention, the first power converter 10 and the second power converter 60 are separate modules having separate controllers 40, 90 and memory devices 42, 92 configured to control operation of the respective power converter. Optionally, a single controller and memory device may be configured to control operation of both power converters.

In operation, the power conversion system is configured to increase the availability of a wind turbine to generate energy. If the wind turbine is configured with an inertial "knee", as previously discussed, the power conversion system is configured to first accelerate the alternator 6 to an initial speed sufficient to begin operation and then to begin transferring the power generated by the alternator 6 to the utility grid. Optionally, the wind turbine may include an anemometer providing a signal corresponding to the wind speed to the controller 40. The controller 40 may operate to accelerate the alternator 6 when the wind speed is greater than the cut-in speed required by the power converter 10 but less than the initial speed required by the wind turbine to begin rotation of the alternator 6. Even if the wind turbine does not have the inertial "knee", the power conversion system may be configured to accelerate the alternator 6 up to the cut-in speed to reduce the amount of time required to begin operation of the wind turbine. Under either operating condition, the power conversion system is configured to operate in a first mode to control the rotational speed of the alternator 6 and in a second operating mode to convert the power supplied from the alternator 6 to the DC bus 12 of the power converter 10.

Subsequent energy storage devices 18 or inverter modules 60 may be connected to the DC bus 12 either to store the power generated by the energy source or to deliver the power generated by the energy source to the utility gird, respectively, when the first power converter 10 is configured to transfer power from the source 6 to the DC bus 12. (see also FIG. 4). The energy storage device 18 may include a DC-to-DC converter to control power between the DC bus 12 and the energy storage device 18. Alternately, the DC-to-DC converter and/or the inverter module 60 may be configured to regulate the voltage present on the DC bus 12 when the power converter 10 is configured to control rotation of the alternator 6. In either operating mode, the controller 40, 90 of each power converter 10, 60 executes one or more control modules which generate gating signals 24, 25, or 74 to selectively connect the switches 20, 21, or 70, respectively, between the DC bus 12 and either the input terminals, $T_1$-$T_3$, or the output 62 according to the desired form of power conversion. According to one embodiment of the invention, a wind turbine may include blades that rotate a low speed drive shaft as a function of the speed of the wind. The low speed drive shaft is input to a gearbox, which, in turn, rotates a high speed drive shaft output as a function of its gearing. The high speed drive shaft rotates the rotor portion of the alternator 6, generating AC voltages, V1-V3, on the stator.

Figure 3:
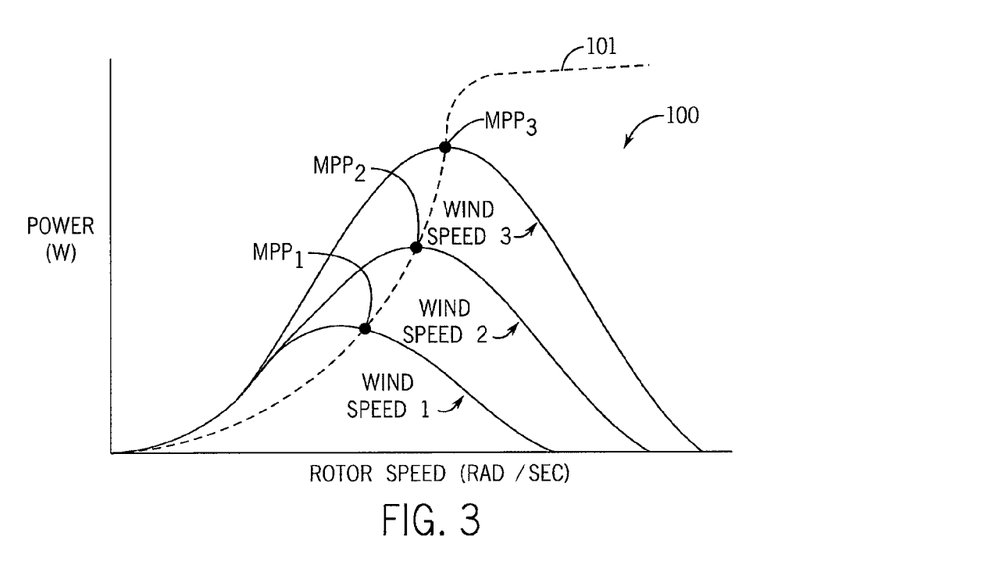
FIG. 3 is a graphical representation of the power generated by a wind turbine as functions of rotor speed and wind speed.

Referring next to FIG. 3, a graph 100 illustrates the relationship between power generated by the alternator 6 as a function of the rotor speed for an exemplary wind turbine operating under varying wind speeds. The speed of the turbine blades may be controlled, for example, by varying the pitch of the blades. Thus, for a constant wind speed, the speed of rotation of the low speed drive shaft and, consequently, the speed of rotation of the rotor in the alternator 6 can be varied. However, the potential exists that the pitch of the blades may not be adjustable at a fast enough rate to respond to varying wind conditions. In addition to, or in lieu of, pitch control, the power converter 10 may help regulate the speed of the alternator 6 by regulating current drawn from the alternator 6 such that a variable braking force is applied to the alternator 6. The electronic control of the current may, therefore, compensate for variations in the wind speed to maintain operation at the maximum power point.

As further illustrated in FIG. 3 by the dashed line 101, operation of an alternator 6 may follow a squared power rule, where the power produced by the turbine increases as the square of the wind speed. For each wind speed, the controller 40 is configured to operate at a maximum power point (MPP), such that the maximum power that may be generated by the alternator at that wind speed is transferred to the DC bus 12. Tracking these maximum power points at the various wind speeds results in the exponential, squared power curve 101 until rated power production occurs. At that point, the controller 40 is configured to limit power production to the rated value to prevent damage to the alternator 6 or to the components of the power converter 10. The controller 40 may be configured to execute control routines both to control the pitch of the blades and to control the current conducted between the alternator 6 and the DC bus 12. Optionally, separate controllers 40 may be used, each executing one of the control modules.

In order to regulate the current drawn from the alternator 6 during normal operating conditions, the controller 40 may implement a synchronous current regulator as is known in the art. A synchronous current regulator receives a current reference and using measured current signals determines a current error value. The synchronous current regulator then determines a desired controlled current to compensate for the current error value. The controller 40 then determines appropriate gating signals, 24 and 25, to selectively connect each phase of the input terminals, T1-T3, to the DC bus 12 to produce the desired controlled current between the alternator 6 and the DC bus 12.

Because the alternator 6 generates AC power, the controller 40 also requires knowledge of the electrical angle of the AC voltages present at the input terminals, T1-T3. When operating above a minimum speed, the controller 40 may determine the electrical angle by detecting the back-emf present at the alternator 6. As the speed of rotation of the alternator increases, the amplitude of the back-emf similarly increases. However, the back-emf is a function of the alternator parameters as well as a function of the rotor speed. Thus, the minimum speed at which the back-emf may be detected is a function of the application. However, the amplitude of the back-emf may typically be reliably detected between about 5% and about 10% of the rated speed of the alternator 6.

Figure 5:
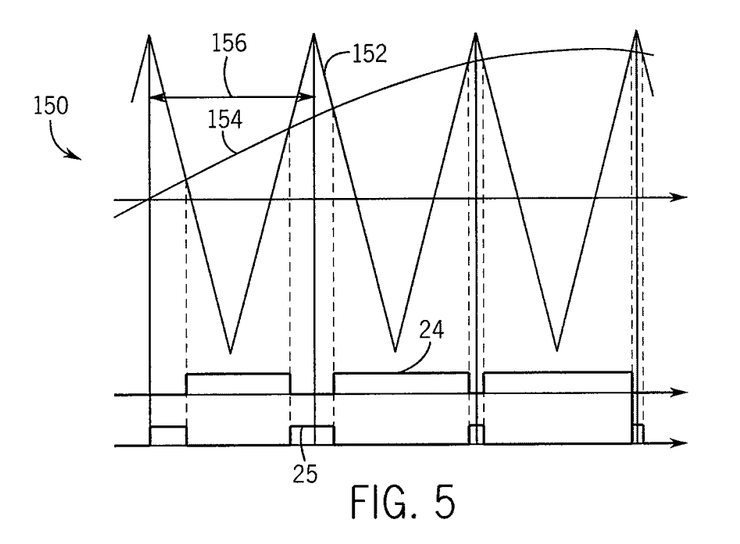
FIG. 5 is a graphical representation of a portion of one modulation period according to one embodiment of the invention.

Referring next to FIG. 5, the synchronous current regulator uses the desired controlled current value and the detected electrical angle of the alternator 6 to generate a voltage reference signal 154 and to generate gating signals 24, 25. In FIG. 5, generation of gating signals 24, 25 for a segment of one cycle for one phase of the AC voltage according to an exemplary sine-triangle PWM modulation technique 150 is illustrated. In the sine-triangle PWM modulation technique 150, a triangular waveform 152 is compared to the voltage reference 154 to generate the gating signals, 24 and 25. One period of the triangular waveform 152 is defined by the switching period 156 of the PWM routine. During the switching period 156, if the voltage reference 154 is greater than the triangular waveform 152, the positive gating signal 24 is set high while the negative gating signal 25 is set low. If the voltage reference 154 is less than the triangular waveform 152, the positive gating signal 24 is set low while the negative gating signal 25 is set high. It is contemplated that other modulation techniques, as would be known to one skilled in the art, may also be used to generate the output voltage, such as space-vector or multi-level switching. Further, the modulation techniques may be implemented by comparing analog signals, as shown in FIG. 4, digital signals, such as a register being incremented up and down, or a combination thereof.

The controller 40 is configured to operate in the two operating modes discussed above, namely a motoring and a generating operating mode for the alternator 6. Thus, it may be desirable to provide a start up control module in the controller 40. The start up control module controls the power converter section 10 as an inverter, treating the alternator 6 as a motor, to accelerate the wind turbine up to an initial speed. Once at the initial speed, the controller 40 can again control the power converter section 10 as a converter and begin transferring power generated by the alternator 6 to the DC bus 12. The alternator 6 of a wind turbine typically does not include an encoder or resolver to provide a feedback signal corresponding to the angular position of the alternator 6. Thus, when the controller 40 operates in the motoring operating mode, an open-loop motor control technique must be employed.

As an AC machine is rotated, a back-emf is established. The magnitude of the back-emf waveform is a function of the speed of rotation of the alternator 6. As the speed of rotation increases, the amplitude of the back-emf generated similarly increases. Using known techniques, such as a phase-locked loop, the controller 40 may periodically sample the back-emf of one or more of the phases to determine the electrical angle of the alternator 6. Knowledge of the electrical angle is necessary during motoring to provide smooth control of the alternator 6 and during generating to regulate the power transferred from the alternator 6 to the DC bus 12.

Controlling the alternator 6 in the motoring mode requires the controller 40 to generate gating signals 24 and 25 to control the positive and negative switches, 20 and 21 respectively, of the power converter 10 according to a modulation technique. Because a wind turbine is typically connected to a utility grid, the system includes both a power converter 10 and an inverter 60 as shown in FIG. 4. However, when the alternator 6 is operated in motoring mode, the power converter 10 is temporarily controlled as an inverter to transfer power from the DC bus 12 to the alternator 6. Similarly, the inverter 60 is temporarily operated as a converter to transfer power from the utility grid to the DC bus 12. Optionally, energy may be transferred from an energy storage device 18 connected to the DC bus 12 via a DC-to-Dc converter for use in driving the alternator 6 as a motor. Thus, either the utility grid or an energy storage device 18 provides the power necessary to drive the alternator 6 as a motor.

Figure 6:
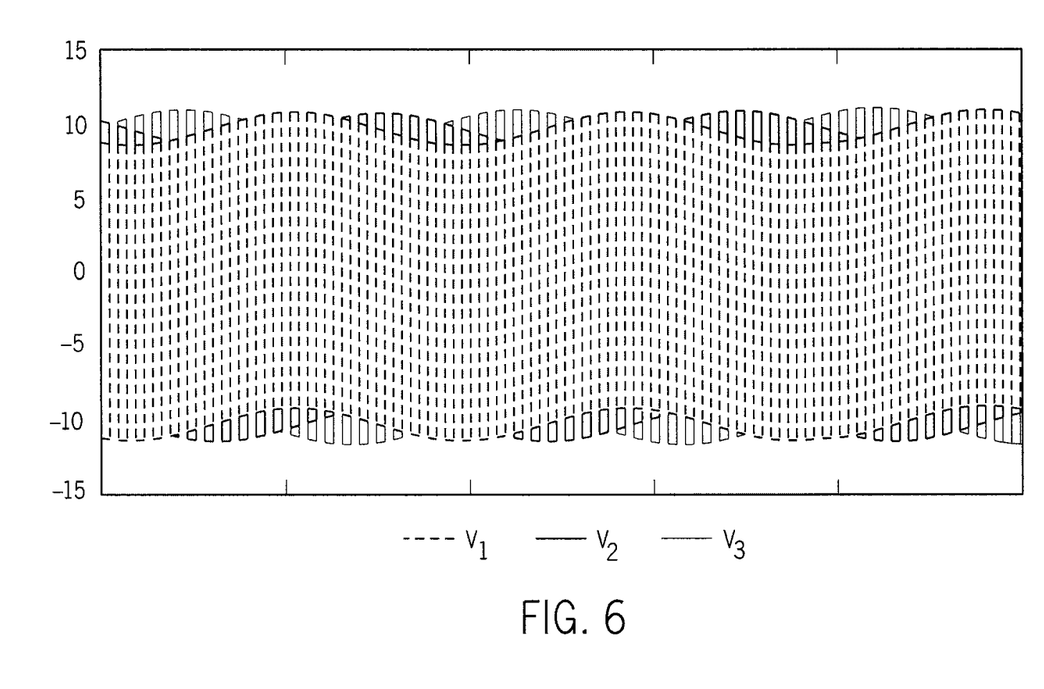
FIG. 6 is a graphical representation of a three phase voltage present at the terminals of the converter of FIG. 1 during operation under continuous pulse width modulation.

Modulation techniques control the positive switches 20 and the negative switches 21 to alternately connect each of the terminals, T1-T3, between either the positive or negative rail, 14 and 16, of the DC bus 12. By controlling the direction of the current flow, the controller 40 causes the alternator 6 to operate either in a motoring or a generating operating mode. Referring next to FIG. 6, the resulting modulated waveforms from alternately connecting each of the terminals, T1-T3, between either the positive or negative rail, 14 and 16, of the DC bus 12 is illustrated. During low speed operation, the amplitude of the modulated waveforms is much greater than the amplitude of the back-emf generated by the alternator 6 and introduces significant noise or uncertainty in attempting to read the value of the back-emf.

Figure 7:
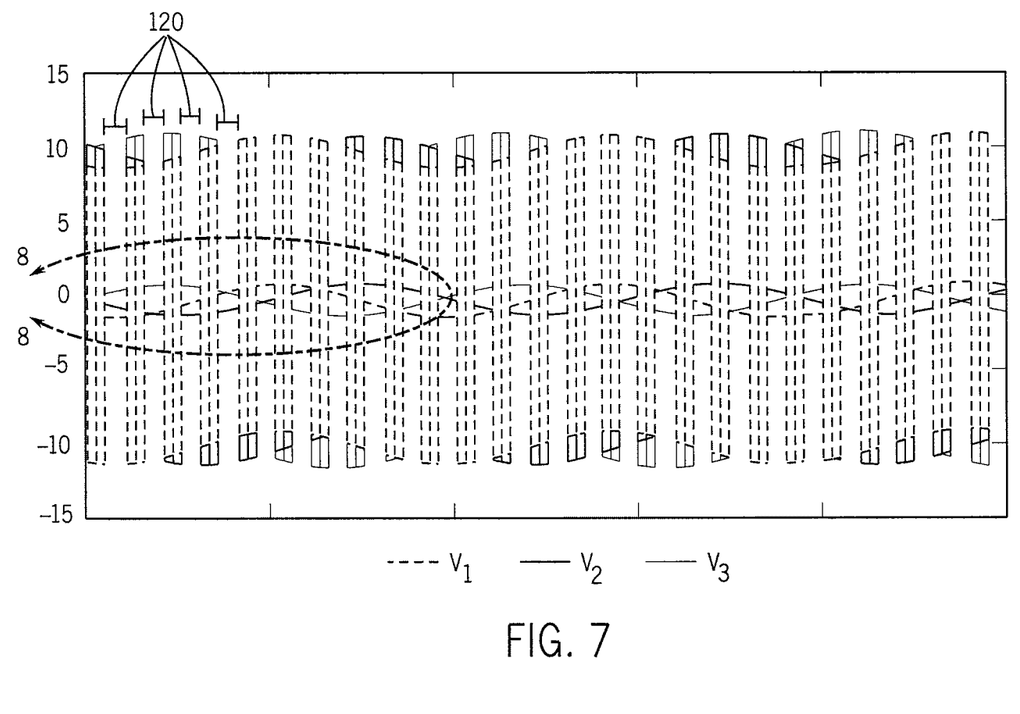
FIG. 7 is a graphical representation of a three phase voltage present at the terminals of the converter of FIG. 1 during operation under pulse width modulation with a periodic blanking time.
Figure 8:
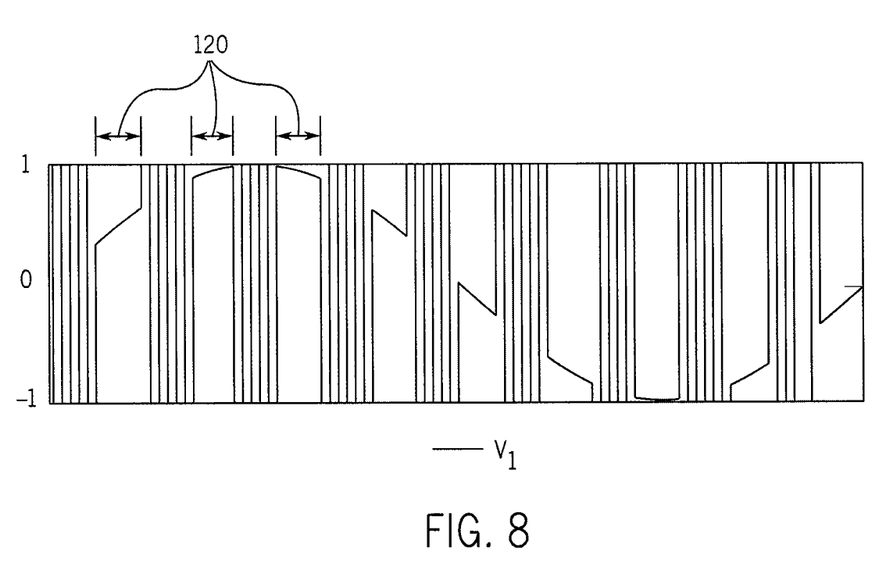
FIG. 8 is a graphical representation of one phase of the three phase voltage of FIG. 7 over one period of the voltage.

Referring next to FIGS. 7 and 8, the controller 40 executes to control the alternator 6 during motoring operation by introducing a short interval, or blanking time 120, during which the modulation is stopped. During the blanking time 120, the controller 40 may read the back-emf voltage without interference from the modulated voltage. The blanking time 120 is short enough such that the inertia of the alternator 6 and the blades of the wind turbine keep the alternator 6 rotating with little or no slowing of the alternator 6. According to one embodiment of the invention, the blanking time is between 1-3 msec and repeated at periodic intervals spaced between 5-20 msec apart. According to a preferred embodiment, the blanking time is about 2 msec and repeated at about 10 msec intervals. During periods of modulation, the power applied to the alternator 6 causes the alternator 6 to accelerate. As the speed of the alternator 6 increases, the amplitude of the back-emf increases. At some point, typically about 5-10% of rated speed, the magnitude of the back-emf is large enough that it may be read during continuous modulation. Thus, the controller 40 controls the alternator 6 from a stop and at low speeds using the blanking time until the alternator 6 reaches a speed at which the back-emf may be continuously monitored. At this speed the controller 40 stops using the blanking time and continuously modulates the voltage to the alternator 6.

When the alternator 6 has reached the desired cut-in speed, the controller 40 switches from the motoring operating mode to the generating operating mode. Consequently, the power converter 10 ceases operation as an inverter and resumes operation as a converter, namely transferring power from the alternator 6 to the DC bus 12. Similarly, the inverter 60 ceases operating as a converter and again operates as an inverter to transfer power from the DC bus 12 to the utility grid.

It is further contemplated that use of the blanking time to read back-emf may be used to extend the range of operation as an alternator during low-speed operation. As previously discussed, knowledge of the electrical angle of the AC power produced by the AC alternator 6 is required for the synchronous current regulator to control power transfer from the alternator 6 to the DC bus 12. As the speed of the rotor slows, the magnitude of the back-emf decreases until the amplitude becomes too low to accurately detect during continuous modulation. Introduction of a blanking time, as described above, allows the power converter 10 to temporarily discontinue modulation and read the back-emf. The electrical angle of the back-emf is determined and corresponding adjustments made to the angle used by the controller 40 to perform modulation. Modulation of the switches, 20 and 21, is resumed at the modified angle to transfer power from the alternator 6 to the DC bus 12.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention

We claim:

1. A power conversion system comprising:
   a set of terminals configured to connect the power conversion system to a polyphase AC machine;
   a DC bus having a positive rail and a negative rail;
   a power converter connected between the set of terminals and the DC bus and configured for bidirectional power transfer between the set of terminals and the DC bus;
   a memory device configured to store a series of instructions; and
   a controller configured to execute the series of instructions to:
   execute a start up control module below a predefined speed, wherein:

the start up control module controls rotation of the AC machine,
the start up control module includes a modulation module configured to convert a voltage on the DC bus to an AC voltage for the AC machine,
the controller is configured to periodically disable the modulation module, and
when the modulation module is disabled, the controller is configured to read a back-emf voltage present on the AC machine; and
execute a current regulator above the predefined speed to transfer power generated by the AC machine to the DC bus.

2. The power conversion system of claim 1 further comprising:
an output configured to be connected to a utility grid; and
an inverter module connected between the output and the DC bus, wherein the inverter module is configured for bidirectional power transfer between the output and the DC bus and wherein the controller is configured to control the inverter module to maintain a desired DC voltage on the DC bus when the start up control module is executing.

3. The power conversion system of claim 1 further comprising:
an energy storage device; and
a second power converter configured to transfer energy between the energy storage device and the DC bus, wherein the controller is configured to control the second power converter to maintain a desired DC voltage on the DC bus when the start up control module is executing.

4. A power conversion system comprising:
a first set of terminals configured to connect the power conversion system to a polyphase AC machine;
a plurality of voltage sensors, each voltage sensor generating a signal corresponding to an amplitude of voltage present at the first set of terminals;
a DC bus having a positive rail and a negative rail;
a plurality of first switches configured to selectively connect the first set of terminals to the DC bus;
a second set of terminals configured to connect to a utility grid;
a plurality of second switches configured to selectively connect the DC bus to the second set of terminals;
a memory device configured to store a series of instructions; and
a controller configured to receive the signal from each of the plurality of voltage sensors and to execute the instructions in a first operating mode and in a second operating mode, wherein:
during the first operating mode:
the controller generates a gating signal for each of the first and second switches to accelerate the AC machine to a predefined speed,
the controller periodically disables the first switches, and
the controller reads the signal from each of the plurality of voltage sensors when the first switches are disabled; and
during the second operating mode:
the controller generates the gating signal for each of the first and second switches to transfer energy generated by the AC machine to the utility grid,
the controller continually controls the first set of switches, and
the controller reads the signal from each of the plurality of voltage sensors in tandem with controlling the first set of switches.

5. The power conversion system of claim 4 wherein during the first operating mode:
the first switches are controlled to provide a multi-phase AC voltage at the first set of terminals, wherein the multi-phase AC voltage has a variable magnitude and a variable frequency to control a speed of the AC machine, and
the second switches are controlled to transfer energy between the utility grid and the DC bus to maintain a substantially constant DC voltage on the DC bus.

6. The power conversion system of claim 4 further comprising:
an energy storage device; and
a DC-to-DC converter connected between the DC bus and the energy storage device, wherein during the first operating mode the DC-to-DC converter is controlled to transfer energy between the energy storage device and the DC bus to maintain a substantially constant DC voltage on the DC bus.

7. The power conversion system of claim 4 wherein the controller is further configured to:
determine a back-emf voltage present at the first set of terminals as a function of the signals read from the voltage sensors, and
determine an electrical angle of the voltage present at the first set of terminals as a function of the back-emf voltage.

8. A method of accelerating a polyphase AC machine for use in a wind turbine up to a predefined initial speed greater than a cut-in speed of the wind turbine, the method comprising the steps of:
controlling a power converter in a first operating mode to execute a modulation module to generate a voltage for the AC machine, wherein the voltage has a variable magnitude and a variable frequency to control a rotational speed of the AC machine;
disabling the modulation module at a periodic interval during execution in the first operating mode;
determining a back-emf voltage present on the AC machine when the modulation module is disabled;
determining the rotational speed of the AC machine as a function of the back-emf voltage; and
controlling the power converter in a second operating mode when the rotational speed is greater than the predefined initial speed, wherein during the second operating mode, the power converter transfers energy from the AC machine to a DC bus in the power converter.

9. A power conversion system for transferring energy generated from an AC generation source to a utility grid, the power conversion system comprising:
a set of terminals configured to connect the power conversion system to the AC generation source;
a DC bus having a positive rail and a negative rail;
a power converter connected between the set of terminals and the DC bus and configured for power transfer between the set of terminals and the DC bus;
a memory device configured to store a series of instructions; and
a controller configured to execute the series of instructions to:
execute a modulation module above a predefined speed for continuous modulation of the power converter to transfer power generated by the AC generation source to the DC bus, and periodically insert a blanking time in coordination with the modulation module below the predefined speed for intermittent modulation of the power converter to transfer power generated by the AC generation source to the DC bus.

\* \* \* \* \*